(12) United States Patent
Jacobs

(10) Patent No.: US 8,606,525 B2
(45) Date of Patent: Dec. 10, 2013

(54) DETERMINING USEFUL LIFE OF A FLUID USING INVENTORY INFORMATION

(75) Inventor: Merrit N. Jacobs, Fairport, NY (US)

(73) Assignee: Ortho-Clinical Diagnostics, Inc., Rochester, NY (US)

( * ) Notice: Subject to any disclaimer, the term of this patent is extended or adjusted under 35 U.S.C. 154(b) by 1706 days.

(21) Appl. No.: 11/285,275

(22) Filed: Nov. 22, 2005

(65) Prior Publication Data

US 2007/0118294 A1    May 24, 2007

(51) Int. Cl.
*G01N 33/50*    (2006.01)
*G01N 33/48*    (2006.01)

(52) U.S. Cl.
USPC .......................................................... 702/19

(58) Field of Classification Search
None
See application file for complete search history.

(56) References Cited

U.S. PATENT DOCUMENTS

| | | | |
|---|---|---|---|
| 4,090,541 A * | 5/1978 | Cammarata et al. | 604/408 |
| 4,495,293 A | 1/1985 | Shaffar | |
| 4,496,293 A | 1/1985 | Nakamura et al. | |
| 4,743,561 A | 5/1988 | Shaffar | |
| 5,314,825 A | 5/1994 | Weyrauch et al. | |
| 5,356,378 A * | 10/1994 | Doan | 604/65 |
| 5,358,691 A | 10/1994 | Clark et al. | |
| 5,646,046 A | 7/1997 | Fischer et al. | |
| 5,885,530 A | 3/1999 | Babson et al. | |
| 6,096,561 A | 8/2000 | Tayi | |
| 7,634,367 B1 * | 12/2009 | Ding et al. | 702/50 |
| 7,748,281 B2 * | 7/2010 | Fukushima et al. | 73/864.13 |
| 2002/0084291 A1 * | 7/2002 | Kelley | 222/456 |
| 2003/0022380 A1 | 1/2003 | Jakubowicz et al. | |
| 2005/0004712 A1 * | 1/2005 | Stevens et al. | 700/266 |
| 2005/0075757 A1 | 4/2005 | Haas et al. | |
| 2005/0110503 A1 * | 5/2005 | Koehler et al. | 324/710 |

FOREIGN PATENT DOCUMENTS

| | | |
|---|---|---|
| EP | 0689038 A2 | 12/1995 |
| EP | 1624303 A2 | 2/2006 |
| JP | 8-43167 C | 2/1977 |
| JP | 2000258432 A | 9/2000 |
| JP | 2005274470 A | 10/2005 |

* cited by examiner

*Primary Examiner* — Jason Sims
(74) *Attorney, Agent, or Firm* — Todd J. Burns

(57) ABSTRACT

A method for determining the remaining time a fluid in a container can be used. The method includes: determining the amount of fluid in the container; and determining the remaining time based on the amount of fluid in the container. Preferably, the step of determining the remaining time is calculated by using the determined amount of fluid and a predetermined first correlation of remaining time vs. amount of fluid in the container. In a preferred embodiment, the fluid is a reagent in a reagent pack used in a diagnostic analyzer. A method for measuring the presence or concentration of an analyte in a sample on an automated diagnostic analyzer includes: providing a reagent storage container on the analyzer; providing a measurement station for taking a measurement of the sample; determining the amount of reagent remaining in a reagent storage container; calculating the remaining time of the reagent by using the determined amount of reagent and a predetermined first correlation of remaining time vs. amount of fluid in the container; if the time the reagent has been in the reagent container is greater than the remaining time, then discarding the reagent, otherwise adding reagent to the sample; and taking a measurement of the sample to determine the presence or concentration of the analyte.

12 Claims, 1 Drawing Sheet

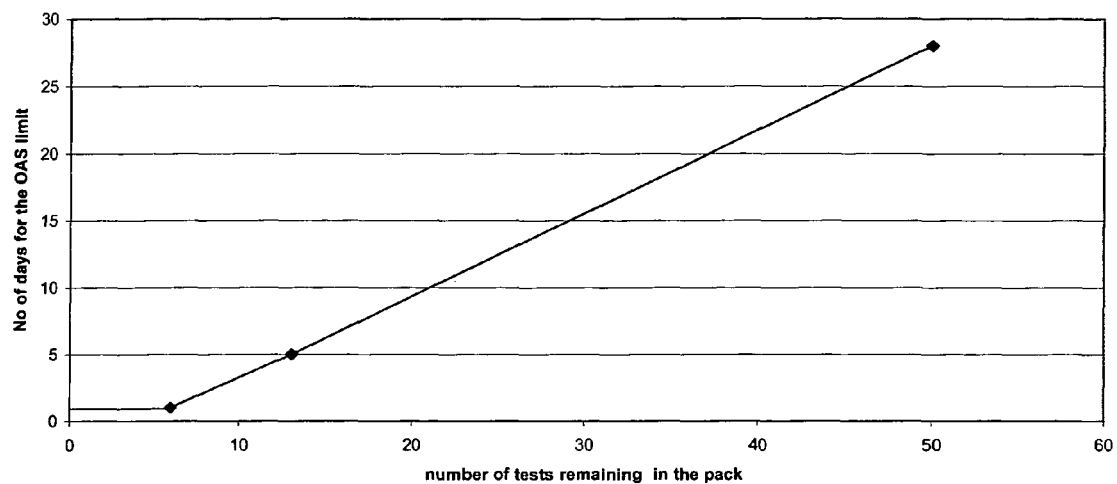

DETERMINING USEFUL LIFE OF A FLUID USING INVENTORY INFORMATION

BACKGROUND OF THE INVENTION

The present invention relates to determining the remaining time a fluid in a container can be used. In particular, the present invention relates determining the remaining time a reagent in a reagent container on an automated diagnostic analyzer can be used.

Known diagnostic analyzers include immunodiagnostic analyzers such as the Vitros® ECi immunodiagnostic analyzer, or clinical chemistry analyzers such as the Vitros® 5,1 FS, both sold by Ortho-Clinical Diagnostics, Inc. All such analyzers are collectively called diagnostic analyzers.

Such analyzers typically use a source of reagent to react with a sample being analyzed to produce a measurable signal that can be determined through conventional means, such as light spectrophotometry, potentiometric or chemiluminescence analysis to name a few. Reagent containers (alternatively called reagent packs) are loaded and stored on the analyzer and are used as needed. The storage of the containers is generally under refrigerated conditions. The amount of reagent is usually based on the number of tests or analysis to be performed. For example, a reagent container may be filled with enough reagent to perform fifty or one hundred tests.

As reagent is used the remaining reagent in the reagent container decreases. As the amount of reagent decreases, the present inventor has found that the stability of the reagent decreases with the corresponding decrease in the amount of reagent. This is believed to be due to several causes such as instability that can result from the fact that lower remaining volume will evaporate more quickly resulting in a faster rate of reagent degradation.

For the foregoing reasons, there is a need for a method of determining the remaining time a fluid can be used in a process, particularly an analytical analysis.

SUMMARY OF THE INVENTION

The present invention is directed to a method that solves the foregoing problems of fluid degradation and determining the remaining time a fluid in a container can be used.

One aspect of the invention is directed to a method for determining the remaining time a fluid in a container can be used, which includes: determining the amount of fluid in the container; and determining the remaining time based on the amount of fluid in the container. Preferably, the step of determining the remaining time is calculated by using the determined amount of fluid and a predetermined first correlation of remaining time vs. amount of fluid in the container. In a preferred embodiment, the fluid is a reagent in a reagent pack used in a diagnostic analyzer.

Another aspect of the invention provides a method for measuring the presence or concentration of an analyte in a sample on an automated diagnostic analyzer, which includes: providing a reagent storage container on the analyzer; providing a measurement station for taking a measurement of the sample; determining the amount of reagent remaining in a reagent storage container; calculating the remaining time of the reagent by using the determined amount of reagent and a predetermined first correlation of remaining time vs. amount of fluid in the container; if the time the reagent has been in the reagent container is greater than the remaining time, then discarding the reagent, otherwise adding reagent to the sample; and taking a measurement of the sample to determine the presence or concentration of the analyte.

Yet another aspect of the invention provides an automated analyzer which includes: a sample supply source; a sample metering station; a reaction vessel; a reagent container containing a reagent; means for determining the amount of reagent remaining in the reagent container; means for calculating the remaining time a fluid in the reagent container can be used by using the determined amount of reagent and a predetermined correlation of remaining time vs. amount of reagent in the reagent storage container; means for calculating if the time the reagent has been in the reagent container is greater than the remaining time, means for alerting an operator if the time the reagent has been in the reagent container is greater than the remaining time; means for adding reagent to the sample; and a measuring instrument for measuring a property of the sample.

Further objects, features and advantages of the present invention will be apparent to those skilled in the art from detailed consideration of the preferred embodiments that follow.

BRIEF DESCRIPTION OF THE DRAWING

The sole FIGURE is a graph of the number of days a reagent can remain on a diagnostic analyzer vs. the number of test remaining the reagent pack.

DETAILED DESCRIPTION OF PREFERRED EMBODIMENTS

The present invention is predicated on the discovery that the amount of remaining time that a fluid, such as a reagent, can be used satisfactorily is dependent, in part, on the amount of fluid remaining in the fluid container. Thus, the present invention provides a method for determining the remaining time a fluid can be satisfactorily used in a process for its intended purpose based on the remaining amount or inventory of fluid remaining in the fluid container, and also based on the length of time the fluid has been in use.

As used herein, "remaining time" is defined as the amount of time a fluid will remain stable and not degrade significantly, such that the fluid can be used with a high degree of confidence that in whatever process the fluid is used, the end result will not be affected by the state of the fluid. For diagnostic purposes, the reagent will remain stable and not degrade significantly, such that the reagent can be used with a high degree of confidence that the resulting assay will not be significantly affected by changes in the reagent. The assay performance may change significantly beyond the remaining time but an alert may be posted advising a user that the reagent has expired.

In order to carry out the present invention, it is necessary to determine the amount of fluid remaining in the container. This can be carried out by any well known method for volume determination, including visual determination either by human vision or a computer vision system. Other means for determining volume can include pressure detection level sensing, capacitive level sensing, ultrasonic sensing or laser sensing. In the field of diagnostic analyzers, the amount of reagent remaining in the reagent container can be determined by subtracting the amount of reagent used for the number of assays already performed, from the original amount of reagent for a predetermined number of analysis. For example, if a reagent pack or container has enough reagent to perform seventy assays and 40 assays have already been performed using reagent in the container, then enough reagent for 30 assays will remain in the reagent pack. Based on the amount of reagent used for each assay, one can determine the amount, such as volume, of reagent remaining in the pack. As a secondary check, the height of the fluid can be verified on the analyzer before the fluid is aspirated for each test in order to ensure the amount remaining is consistent with the calculated number of tests in the reagent pack.

The remaining time may then be determined based on the amount of fluid remaining in the container. Preferably, this is done based on a first predetermined correlation between the remaining time the fluid can be used versus the amount of fluid remaining in the container. The first correlation can be determined experimentally by comparing the remaining fluid in the container with the amount of time the fluid can still be satisfactorily used. For example, if it is experimentally determined that 100 ml of fluid in a container has a remaining time of 100 days, 50 ml has a remaining time of 50 days and 25 ml has a remaining time of 25 days, etc., then for the same type of fluid (or similar fluid) the remaining time can be determined from the above correlation. While the above example shows a linear correlation, the relationship may be non-linear, e.g., exponential.

In a preferred embodiment, determining the remaining time also depends on a second correlation between a normal remaining time a fluid can be used (not taking into account the first correlation described above) versus the length of time the fluid has been in use. The total time a reagent or other fluid can be used is based on its normal expiration without any change in its initial volume. Thus, the normal remaining amount of time a fluid can be used is the total time the fluid can be used minus the length of time the fluid has been in use.

Use of both the first and second correlation can be described as a dual clock approach of normal remaining time before normal expiration and the reduced remaining time associated with the inventory volume described above. The volume or first correlation described above always reduces the remaining time that the reagent can be used before it is considered expired. The clock for the second correlation or normal expiration starts when the fluid is first used, e.g., when the reagent is installed on the analyzer and opened. If the fluid is never used it will have the longest available life before expiration. Using the reagent both reduces the number of tests remaining and the available time that it can still be safely used on the system based on the first correlation. For example, in the case of a diagnostic analyzer, when the reagent is installed on the analyzer and opened, it may have a normal usable life of 7 days. Once reagent is drawn out of the reagent container or pack, the remaining time will begin to be reduced based on the first correlation described above. If a reagent pack having an normal opened life of 7 days is installed on an analyzer and not used for 6 days and 23 hours, based on the second correlation it will only have one hour of remaining life regardless of the amount of reagent that has been withdrawn from the reagent pack. Thus, the remaining time will either be bounded by the volume/remaining time correlation (i.e., the first correlation) and/or the normal expiration of the reagent once it is installed on the analyzer (i.e., the second correlation).

Another useful illustration between remaining time based on normal expiration (i.e., the second correlation) and the remaining time based on inventory volume (i.e., the first correlation) is with potentiometric assays or ion-selective electrode ("ISE") assays. For these assays one would track the reference fluid volume and reduce the remaining life before expiration as a function of both normal expiration time and reduced time associated with reduced inventory volume. The value in this is that very slight evaporation of the reference fluid causes the ISE assays, such as sodium, to drift. As the reference fluid becomes more concentrated the sodium assay drifts negative. A user that uses the entire container of reagent except for the last few tests and then lets it stay on the analyzer in this state until its normal expiration, e.g., 24 hours, will see more drift than a user that uses the reference fluid gradually across a 24 hour time frame. This is based on the remaining time inventory or first correlation described above. Use of the relationship to volume may extend the allowable life beyond the current 24 hour normal expiration because the normal expiration was established to ensure that the unusual user that quickly uses almost all the reagent and then lets it sit for many hours will still have good results.

The first correlation is also shown in the sole FIGURE. In the FIGURE, the remaining days a reagent can be used in a valproic acid assay is plotted on the y-axis (the number of remaining days is also called "OAS limit" which stands for on analyzer stability limit), while the number of assays or tests (i.e., the amount of reagent) is plotted on the x-axis. Thus, from this graphical correlation, the remaining time for a particular amount of reagent in the reagent pack can readily be determined. As shown in the FIGURE, there is a straight line linear regression from 50 test remaining in the pack to approximately 5 tests. At this point, the curve becomes flat and the OAS remains the same from 5 to 1 tests. For other assays, the relationship between amount of reagent remaining and stability may be significantly different from the one shown in the FIGURE. For example, the stability at the start of using the reagent may be relatively stable for several tests and then drop off dramatically once a certain volume of reagent has been used. This may be related to the geometry of the container causing variation in the surface area of the fluid driving different evaporation rates at different inventory points. In other examples, just the opposite may occur. That is, at the start of using the reagent, the stability may drop off dramatically and quickly stabilize at a lower OAS limit. However, in typical assays, the shape of the curve will be similar to that shown in the FIGURE. The shape of the curve can be determined through experimentation and loaded onto analyzer computer (or remote computer), such as through the analyzer data disk (ADD). The shape of the curve may be different for different lots of the same reagent.

Determining the remaining time can either be carried out by hand using a graph of remaining time versus amount of fluid. More preferably, the correlation data can be loaded onto a computer and the computer calculates the remaining time based on the input amount of fluid and the length of use of the fluid. In many applications the amount of fluid and length of time the fluid has been in use is normally monitored as the fluid is used. The computer monitoring the remaining time can be located where the fluid is located or located remotely. For example, in an industrial process, the computer is preferably located in a control room, which controls the entire process and is remote from a bulk tank holding the fluid.

In the preferred field of diagnostic analyzers, the computer may be located on the analyzer. Alternatively, the computer may be located remotely from the analyzer, such as a computer controlling an automated laboratory through a laboratory information systems (LIS), or even more remotely through an intranet system or over the internet. LIS and other computer architecture are well known in the art. See for example, U.S. Published Patent Application US 2005/0075757 A1 published Apr. 7, 2005 which is incorporated by reference in its entirety.

In some instances, it may be particularly useful for the analyzer to be connected through the internet, possibly via a LIS, to a supplier/manufacturer of reagents. In such an instance, the supplier/manufacturer could constantly monitor the volume of reagent remaining and alert the user of the analyzer when the remaining time for the reagent had reached a point, where the residual reagent in the container must be discarded and fresh reagent installed onto the analyzer. Via the internet connection, an option would be for the manufacturer/supplier to ship additional reagent when the remaining time the reagent could be used is low.

In the field on in vitro diagnostics, the present inventor has found that the present invention works particularly well with assays for the therapeutic drug monitoring ("TDM") family, drugs of abuse ("DAU") family, and ion selective electrode (ISE) assays.

The present invention also provides a method for measuring the presence or concentration of an analyte in a sample. This aspect of the invention uses steps which are, per se, known in the art. Included with these known steps is the inventive method of determining the remaining time a reagent in a reagent pack can be used. In particular, a sample is loaded onto an automated diagnostic analyzer. A specific amount of sample, e.g., 5 ul, is aspirated by an aspirate/dispense probe and dispensed into another container, which may or may not be the container in which the measurement is conducted.

A predetermined quantity of reagent is then aspirated from a reagent pack. In some systems, the reagent may be added first, whereas in other systems the sample is added before the reagent. Whether or not the reagent is still usable is determined according to the method described above. After the reagent is added, the sample/reagent mixture is optionally incubated at a predetermined time and temperature. One or more optional dilutions may also be carried out. The sample reagent mixture is then measured using a measuring instrument such as a photometer or spectrophotometer. In immunodiagnostic assays extra steps of bound free separation step and addition of signal reagent for chemiluminescence are required before measurement with a luminometer. For potentiometric assays only the addition of sample and reference fluid to the same slide but different electrode is required. The voltage is then measured with an electrometer. In some instances, a wash step is required to remove the unbound fraction and then a signal reagent will be added before measurement. Based on the measurement, the amount of analyte in the sample can be determined. Spectrophotometric absorbance assays can include end-point reaction analysis and rate of reaction analysis. Other types of measurements can include turbidimetric assays, nephelometric assays, radiative energy attenuation assays (such as those described in U.S. Pat. Nos. 4,496,293 and 4,743,561 and incorporated herein by reference), ion capture assays, colorimetric assays, fluorometric assays, electrochemical detection systems, potentiometric detection systems, and immunoassays. Some or all of these techniques can be done with classic wet chemistries; ion-specific electrode analysis (ISE); thin film formatted "dry" chemistries; bead and tube formats or microtiter plates; and the use of magnetic particles. U.S. Pat. No. 5,885,530 provides a description useful for understanding the operation of a typical automated analyzer for conducting immunoassays in a bead and tube format and is incorporated herein by reference.

The present invention also includes a diagnostic analyzer having means for determining the amount of fluid remaining in the reagent. The means for determining the amount of fluid are described above are not repeated for the sake of brevity. Analyzers, themselves, are known in the art. See for example, U.S. Published Patent Application No. US 2003/0022380 A1, and U.S. Pat. Nos. 6,096,561 and 5,358,691 all of which are incorporated by reference in their entireties.

The method for determining the remaining time of a fluid can be implemented by a computer program, having computer readable program code, interfacing with the computer controller of the analyzer as is known in the art.

It will be apparent to those skilled in the art that various modifications and variations can be made to the compounds, compositions and processes of this invention. Thus, it is intended that the present invention cover such modifications and variations, provided they come within the scope of the appended claims and their equivalents.

The disclosure of all publications cited above are expressly incorporated herein by reference in their entireties to the same extent as if each were incorporated by reference individually.

I claim:

1. A method for determining the remaining time a reagent in a diagnostic analyzer reagent pack can be used in a diagnostic analyzer, comprising:
    determining the amount of reagent in the reagent pack;
    providing a predetermined first correlation of remaining time vs. amount of reagent in the reagent pack;
    determining the total time the reagent can be used without any change in the volume of the reagent;
    subtracting the amount of time the reagent has been in use from the total time to arrive at a normal remaining time the reagent can be used which provides a second correlation of normal remaining time the reagent can be used versus the length of time the reagent has been in use; and
    determining the remaining time based on the first correlation, the second correlation and the amount of reagent in the reagent pack;
    wherein the first correlation is stored on a computer and the computer calculates the remaining time based on the input of the first correlation and the volume of reagent in the reagent pack, and wherein the reagent is aspirated from the reagent pack with an aspirate/dispense probe.

2. A method as claimed in claim 1, wherein the amount of reagent is expressed in units of volume.

3. A method as claimed in claim 1, wherein the amount of reagent is expressed in units of weight.

4. A method as claimed in claim 1, wherein the computer controlling the method is part of a diagnostic analyzer.

5. A method as claimed in claim 1, wherein the computer controlling the method is remote from a diagnostic analyzer.

6. A method as claimed in claim 5, wherein the diagnostic analyzer communicates with the computer through one of an intranet, laboratory information system, or internet.

7. A method as claimed in claim 5, wherein the diagnostic analyzer communicates with the computer through the internet and the computer sends a warning signal when the remaining time is exceeded.

8. A method as claimed in claim 7, wherein the computer is at the reagent supplier.

9. A method as claimed in claim 1, wherein the amount of reagent is determined by the number of tests remaining in the container.

10. A method as claimed in claim 9, wherein the amount of reagent is determined by a known amount of reagent for a predetermined number of analysis minus the number of analysis already performed.

11. A method as claimed in claim 1, wherein the amount is determined by the volume of fluid in the reagent pack.

12. A method as claimed in claim 1, wherein the diagnostic analyzer communicates with the computer through one of an intranet, laboratory information system, or internet.

* * * * *